United States Patent
Peng et al.

(10) Patent No.: US 10,053,985 B1
(45) Date of Patent: Aug. 21, 2018

(54) REAL-TIME WATER-LEVEL MONITORING SYSTEM FOR DUMPING SITE OF OPEN-PIT COAL MINE, AND METHODS OF ESTABLISHMENT AND USE OF THE SAME

(71) Applicant: China University of Mining & Technology-Beijing, Beijing (CN)

(72) Inventors: Suping Peng, Beijing (CN); Feisheng Feng, Beijing (CN); Pingjie Fu, Beijing (CN); Wenfeng Du, Beijing (CN); Pan Wang, Beijing (CN)

(73) Assignee: CHINA UNIVERSITY OF MINING & TECHNOLOGY-BEIJING, Beijing (CN)

( * ) Notice: Subject to any disclaimer, the term of this patent is extended or adjusted under 35 U.S.C. 154(b) by 0 days.

(21) Appl. No.: 15/686,593

(22) Filed: Aug. 25, 2017

(30) Foreign Application Priority Data

Mar. 24, 2017 (CN) .......................... 2017 1 0182956

(51) Int. Cl.
*B09B 1/00* (2006.01)
*E21F 17/18* (2006.01)
(Continued)

(52) U.S. Cl.
CPC ............ *E21F 17/18* (2013.01); *A01G 25/167* (2013.01); *B09B 1/00* (2013.01); *B09B 1/004* (2013.01);
(Continued)

(58) Field of Classification Search
CPC ......... B09B 1/00; B09B 1/004; E02D 31/004; E21F 17/18; A01G 25/167; C08G 63/78; E21C 41/26; G01F 23/18; G01N 33/246
(Continued)

(56) References Cited

U.S. PATENT DOCUMENTS 4,166,709 A * 9/1979 Valiga .................... E02D 31/004
405/129.55
4,464,081 A * 8/1984 Hillier ....................... B09B 1/00
405/128.15
(Continued)

FOREIGN PATENT DOCUMENTS

CN       2158083 Y      3/1994
CN    101942989 A       1/2011
(Continued)

OTHER PUBLICATIONS

Mikic, M., Urosevic, D., Gardic, V., Petrovic, B., Monitoring the quality of water, air, and soil of the ash and slag landfill of TPP Gacko Cassette III, Phase 1 and 2, Jan. 2014, (Year: 2014).*
(Continued)

*Primary Examiner* — Carib A Oquendo
(74) *Attorney, Agent, or Firm* — Locke Lord LLP; Tim Tingkang Xia, Esq.

(57) ABSTRACT

The invention discloses a real-time water-level monitoring system for a dumping site of an open-pit coal mine. The dumping site of the open-pit coal mine comprises an aboveground part and an underground part, where the aboveground part is a stacking site (1) located above an original ground surface. The real-time water-level monitoring system for a dumping site of an open-pit coal mine comprises a first measuring well (2) and a second measuring well (3), where the first measuring well (2) is arranged vertically in the center of the stacking site (1), and the second measuring well (3) includes a vertical section (301), a horizontal section (302), and a free section (303) connected in sequence; and a first water-impermeable layer (4), a second water-impermeable layer (5), and a third water-impermeable layer (6) are provided internally in the stacking site (1).

9 Claims, 9 Drawing Sheets

(51) Int. Cl.
*G01F 23/18* (2006.01)
*G01N 33/24* (2006.01)
*E21C 41/26* (2006.01)
*A01G 25/16* (2006.01)
*C08G 63/78* (2006.01)

(52) U.S. Cl.
CPC .............. *B09B 1/006* (2013.01); *C08G 63/78* (2013.01); *E21C 41/26* (2013.01); *G01F 23/18* (2013.01); *G01N 33/246* (2013.01)

(58) Field of Classification Search
USPC ..... 405/129.1, 129.45, 129.5, 129.55, 129.6, 405/129.7, 129.75, 129.8, 1, 29.85, 405/129.95
See application file for complete search history.

(56) References Cited

U.S. PATENT DOCUMENTS

| | | | | |
|---|---|---|---|---|
| 5,054,962 A | * | 10/1991 | Bahnmuller | B09B 1/004 405/129.6 |
| 5,201,609 A | * | 4/1993 | Johnson | B09B 1/00 405/129.7 |
| 5,215,409 A | * | 6/1993 | Jax | B09B 1/00 405/129.5 |
| 5,362,397 A | * | 11/1994 | Cyr | B09C 1/10 210/610 |
| 5,401,118 A | * | 3/1995 | Kramer | E02D 31/004 405/129.45 |
| 2001/0005812 A1 | * | 6/2001 | Brookshire | B09B 1/00 702/6 |
| 2005/0207848 A1 | * | 9/2005 | Kunerth | G01L 19/083 405/129.1 |
| 2006/0008325 A1 | * | 1/2006 | Ianniello | B09B 1/00 405/129.1 |
| 2011/0283821 A1 | * | 11/2011 | Ober | G01N 33/0031 73/866.1 |
| 2012/0297928 A1 | * | 11/2012 | Lang | C22B 3/02 75/386 |
| 2015/0217347 A1 | * | 8/2015 | Mullins | B09B 1/00 405/129.85 |

FOREIGN PATENT DOCUMENTS

| | | |
|---|---|---|
| CN | 102830052 A | 12/2012 |
| CN | 103352458 A | 10/2013 |
| CN | 105672094 A | 6/2016 |
| CN | 206020226 U | 3/2017 |

OTHER PUBLICATIONS

Lin Li et al., The deformation characteristics and prevention measures of dump slope in the Baorixile Open Pit Coal Mine, 2009, 5.
Yufu Liu et al., Study on the stability of seepage dump in the Haerwusu Open Pit Coal Mine, 2013, 2.

* cited by examiner

REAL-TIME WATER-LEVEL MONITORING SYSTEM FOR DUMPING SITE OF OPEN-PIT COAL MINE, AND METHODS OF ESTABLISHMENT AND USE OF THE SAME

CROSS-REFERENCE TO RELATED APPLICATION

This application claims priority to and benefit of, under 35 U.S.C. § 119(a), Chinese Patent Application No. 201710182956.1 filed on Mar. 24, 2017 in the State Intellectual Property Office of P.R. China, which is incorporated herein by reference in its entirety.

FIELD OF THE INVENTION

The present invention relates to the technical field of mines, and in particular to a real-time water-level monitoring system for a dumping site of an open-pit coal mine and methods of establishment and use of the same.

BACKGROUND OF THE INVENTION

Open-pit coal mining involves directly peeling off the topsoil and a strata overlying a coal seam, so the coal seam is exposed and then exploited. The stripped rock and soil are stacked in layers inside and outside of a mining area, to form a dumping site. A large-size dumping site is an artificially piled giant body formed by stacking the mixed soil and rock in the mining area. During the formation of a large-size dumping site by stacking, the changes in local water level and water quality of the dumping site are critical factors in the regional environmental assessment and in the early warning during the safety production of a coal mine.

The formation process of the dumping site is practically a mining process of an open-pit mine; however, few relevant studies are available now. The water level is investigated by some work teams by arranging several measuring wells in an area around the dumping site. However, this mode of arrangement requires multiple measuring wells, and the cost is high. Moreover, the actual changes in water level and water quality of the dumping site are not determined directly, which is inexact for scientific research, and the changing tread of the water level and water quality from the center of the dumping site to surrounding areas cannot be determined. Finally, real-time monitoring of the changes of water level and quality during the formation process of the dumping site from small to large, that is, the whole process from the mining of the mining region to the formation of the dumping site by mining, is not really achieved at present. However, this data is of great reference significance for scientific research, environmental assessment and early warning in safe production of a coal mine. The dumping site of the open-pit coal mine has the characteristics of "heavy rain, serious slippery; light rain, moderate slippery; and no rain, no slippery", so it is very important to monitor the change of water level in the dumping site in real time, as far as the stability of the dumping site is concerned.

The difficulties in real-time monitoring of the changes of water level mainly include the following.

1. During the formation process of the dumping site, the ground surface is elevated from low to high, and thus the height of the measuring well will be gradually increased dumping site. It is a difficulty to realize the safe and stable increase of the height of the measuring well, and ensure the stable measurement and transmission of the data.

2. The dumping site mainly includes two regions in a longitudinal direction. One is an aboveground region that is a stacking site. The water in this region is mainly replenished by surface water, and the changes of water level is high and greatly affected by the weather, and has important impact on the safety of the dumping site. The other region is an underground region, and the water level in this region is affected by the drainage of the pit, and directly correlates with the drainage and gushing-out of water from the pit. The water quality is also an important reference data.

SUMMARY OF THE INVENTION

The technical problem to be solved in the present invention is how to overcome the difficulties existing in the prior art to monitor the changes in regional water level and water quality of a dumping site during the formation of the dumping site, that is, before, during, and after the mining of an open-pit coal mine. In this regard, the present invention provides a real-time water-level monitoring system for a dumping site of an open-pit coal mine that is simple in structure, low in cost, and convenient for operation.

The real-time water-level monitoring system for a dumping site of an open-pit coal mine according to the present invention differs from the prior art as follows.

During the formation process of the dumping site, the ground surface is elevated from low to high, and thus the height of a measuring well is gradually increased. By means of the system of the present invention, the safe and stable increase of the height of the monitoring well is achieved, and the stable measurement and transmission of the data is ensured.

The dumping site mainly includes two regions in a longitudinal direction. One is an aboveground region that is a stacking site. The water in this region is mainly replenished by surface water, and the changes of water level is high and greatly affected by the weather, and has important impact on the safety of the dumping site. The other region is an underground region, and the water level in this region is affected by the drainage of the pit, and directly correlates with the drainage and gushing-out of water from the pit. By the system of the present invention, the detection of water level in both the aboveground and underground part is achieved. In the real-time water-level monitoring system for a dumping site of an open-pit coal mine according to the present invention, a mining and stacking form are designed based on the regular pattern of coal mining, a water retaining means is added, and suitable species of plants are grown, to achieve the intelligent online monitoring and the scientific and accurate monitoring of water resources, while the work intensity of the workers is reduced and the safety of workers during working is ensured. Moreover, the stability of the power line and thus the stability of the system are ensured by the design of the cable tube.

In a preferred embodiment, because the dumping site is high, vast and strongly hydrophobic, so the rainfall and the manually sprayed water are soon absorbed and sink down to a level below the stacking site. The valuable water resource above the stacking site is effectively protected by the first water-impermeable layer, through which the full growth of the plant and the maximum utilization of the water resources are ensured. Particularly, the plants with a long root system are effective for the sand and water retention in the topsoil layer. The first water-impermeable layer is effectively and reasonably designed. The safety of overlying topsoil layer is ensured by a plurality of anti-sliding plates arranged in parallel at both end, so no risk of landslide exists. A plurality of first soil humidity sensors is fixed on the first water-impermeable layer, which can provide real-time scientific data support for the growth environment of plants. Because the dumping site is high, vast and strongly water repellent, the first water-impermeable layer is arranged. However, the soil resource in the topsoil layer is valuable and strongly hydrophobic, so a plurality of second water-impermeable layers are provided in and below the topsoil layer, and plants with a short root system are grown in the topsoil layer above the second water-impermeable layer. In this manner, reasonable distribution of root length is formed with the first water-impermeable layer, the valuable soil resource in the topsoil layer is made fully use, and the region becomes an occurrence region enveloping vapor and containing water. The water resource at the slope is reserved by the third water-impermeable layer, and the safety of the slop is improved by the interval design and the anti-sliding design. At the same time, the full and effective growth of the plants further increases the safety of the slope. As such, a virtuous circle is formed. The use of the three water-impermeable layers in combination can fully retain water, promote the plant growth, and increase the stability of the stacking site. Based on the three water-impermeable layers, the soil humidity sensors are evenly distributed in various regions of the stacking site, thus fully ensuring the scientific analysis of the growth environment of plants.

The soil monitoring tube is 0.7 m high. According to the root length of plants that is 200-300 mm in the case of a short root system and 300-800 mm in the case of a long root system, the soil temperature and humidity in an extent of 200-800 mm in the longitudinal direction are monitored, thereby achieving the full and effective monitoring of temperature and humidity of the soil resource. By means of the intelligent water spraying means, the accurate water replenishment to the soil is achieved, such that the usage of water is greatly improved, and the usage of soil is also greatly improved.

The system of the present invention has the advantages of simple structure, simple method of use, and remarkable effect, and fills the gaps in this field. The real-time water-level monitoring system for a dumping site of an open-pit coal mine of the present invention will now be described in further detail with reference to the accompanying drawings.

BRIEF DESCRIPTION OF THE DRAWINGS

Additional objectives, functions and advantages of the present invention will be set forth in the description of embodiments which follow, with reference to the accompanying drawings in which.

DETAILED DESCRIPTION OF THE INVENTION

Figure 1:
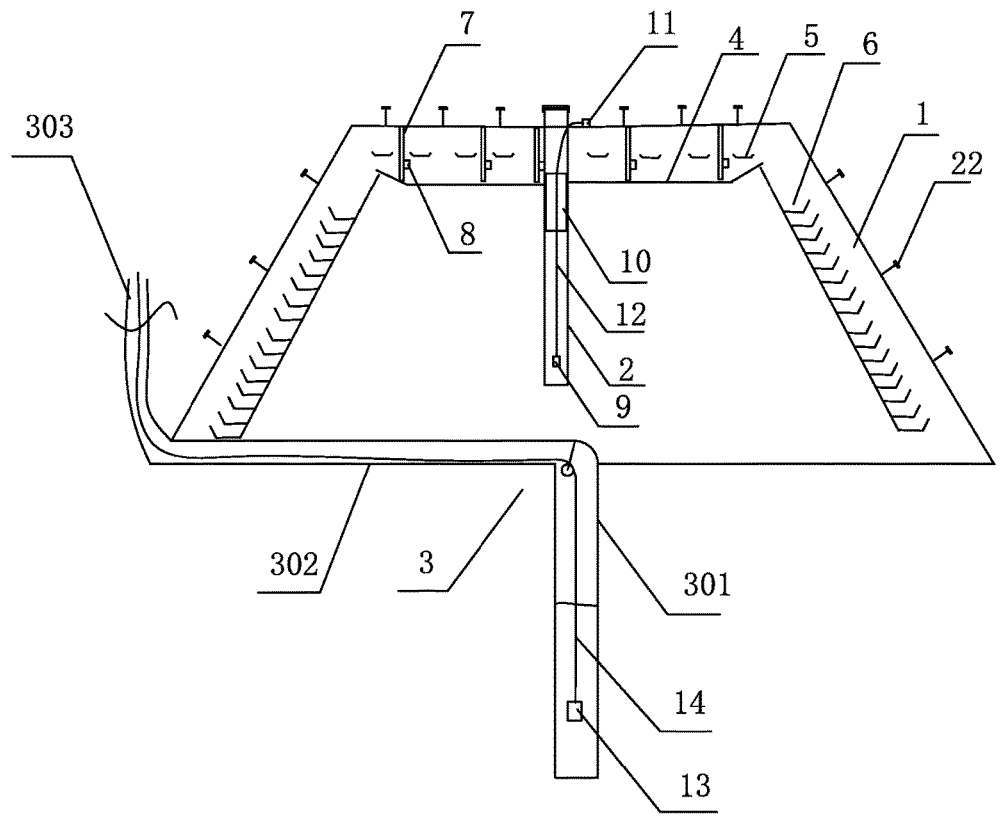
FIG. 1 is a schematic view showing the structure of a real-time water-level monitoring system for a dumping site of an open-pit coal mine according to the present invention.
Figure 2:
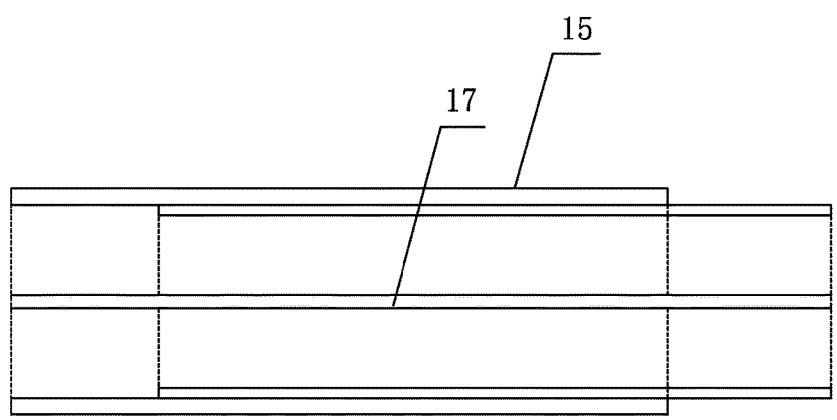
FIG. 2 is a schematic view showing the structure of a self-sealing sleeve in the present invention.
Figure 3:
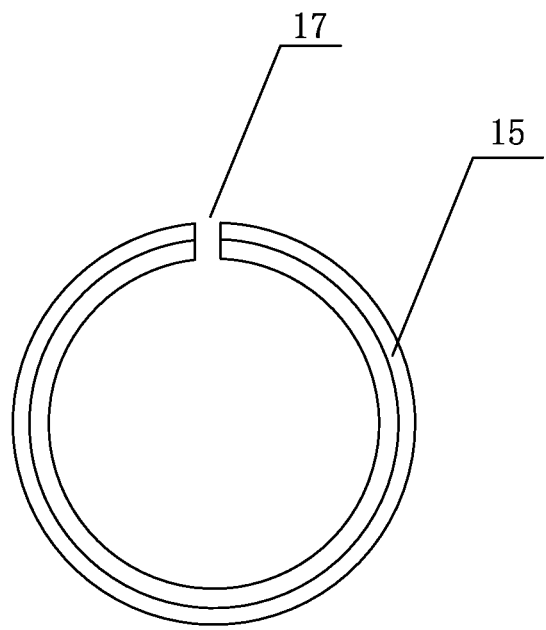
FIG. 3 is a schematic top view showing the structure of the self-sealing sleeve in the present invention.
Figure 4:
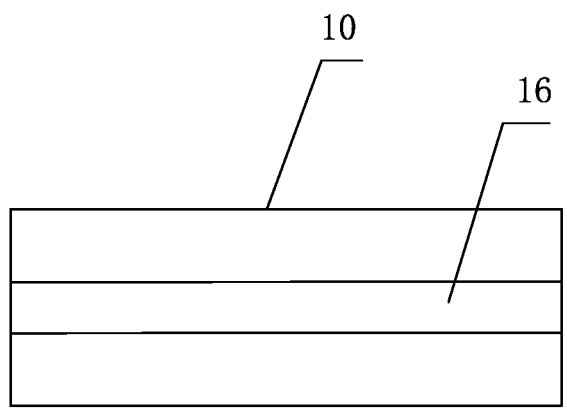
FIG. 4 is a schematic view showing the structure of a fixing sleeve in the present invention.
Figure 5:
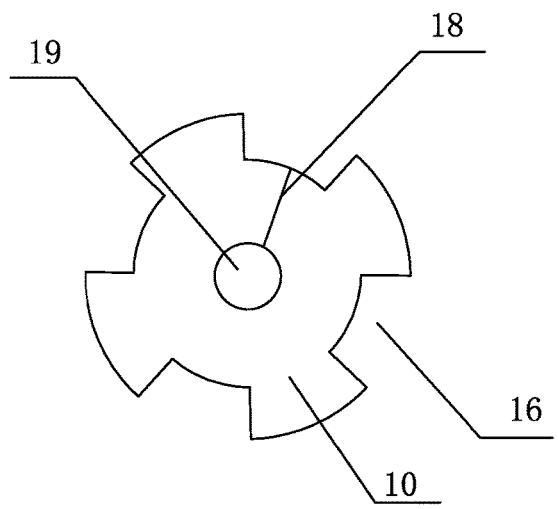
FIG. 5 is a schematic top view showing the structure of the fixing sleeve in the present invention.
Figure 6:
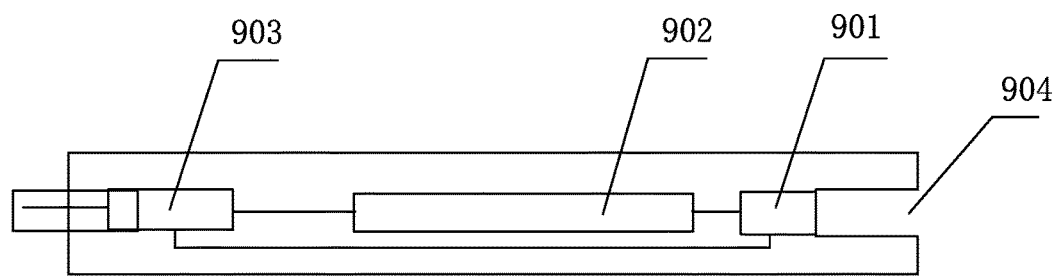
FIG. 6 is a schematic view showing the structure of a first water-level sensor and a second water-level sensor in the present invention.
Figure 7:
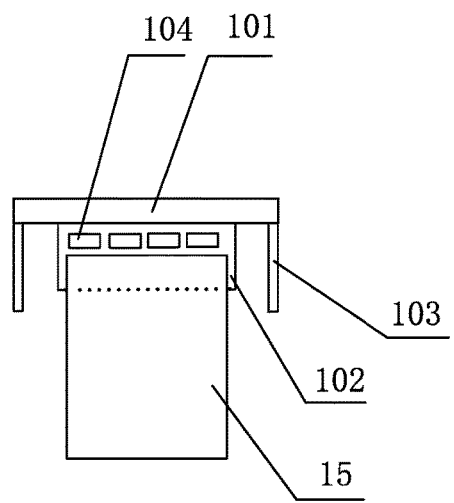
FIG. 7 is a schematic view showing the structure of a breathable water-proof cover in Embodiment 1 of the present invention.
Figure 9:
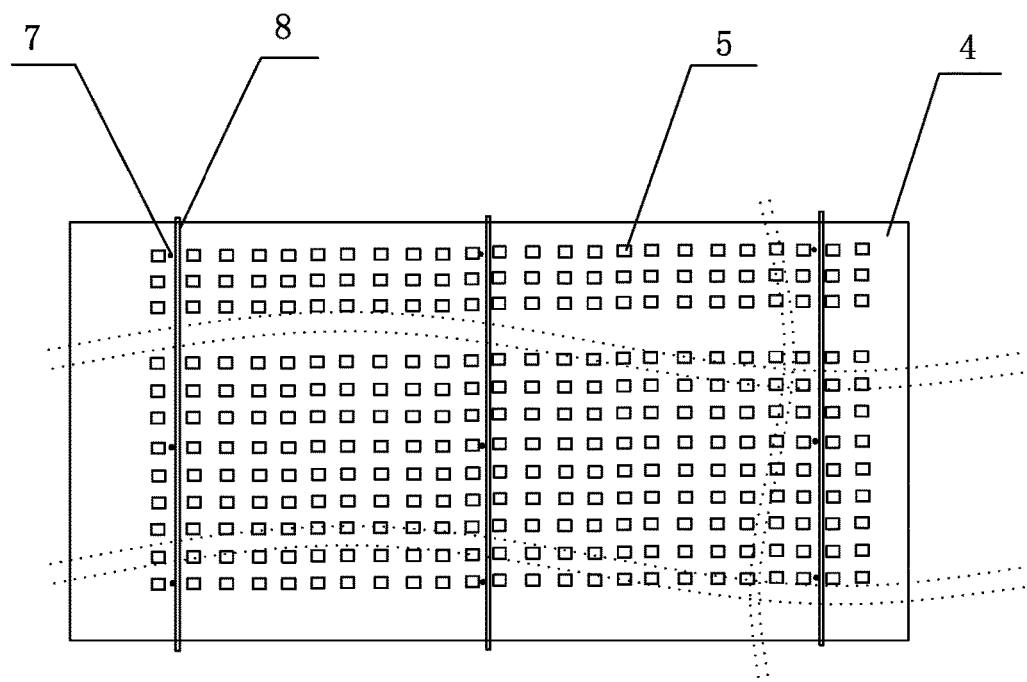
FIG. 9 is a schematic top view showing a top of a stacking site in the present invention.
Figure 10:
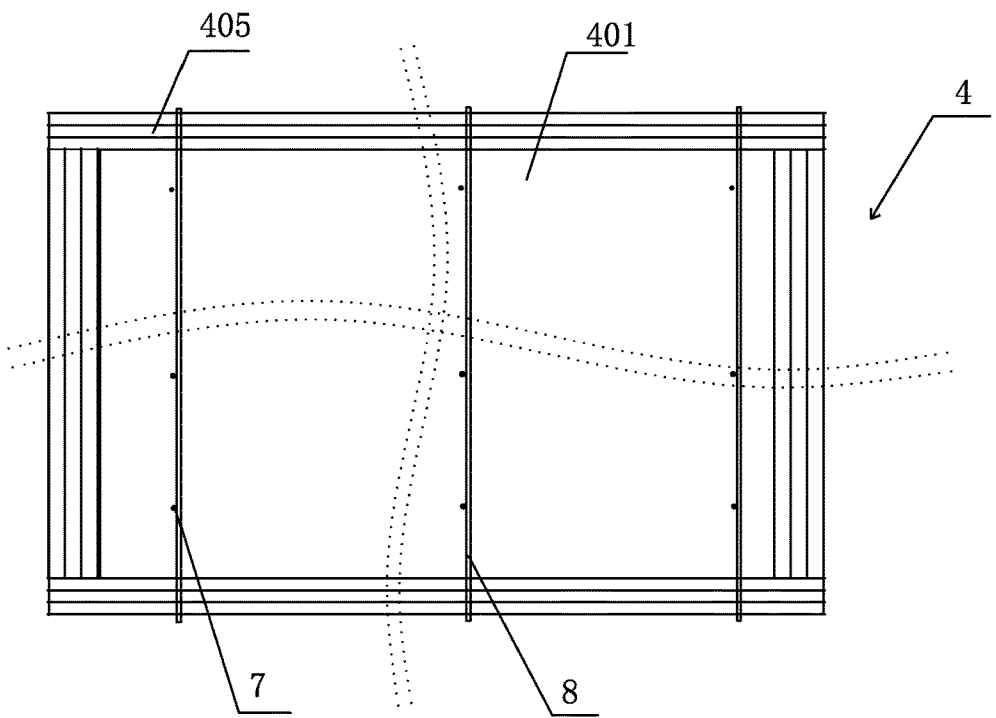
FIG. 10 is a schematic top view showing the structure of a first water-impermeable layer in the present invention.
Figure 11:
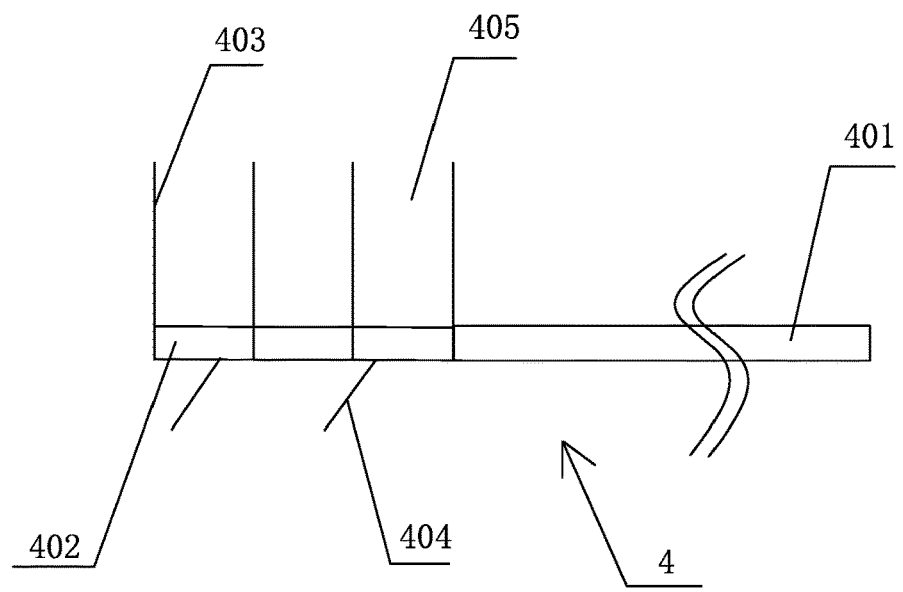
FIG. 11 is a schematic cross-sectional side view showing the structure of the first water-impermeable layer in the present invention.
Figure 12:
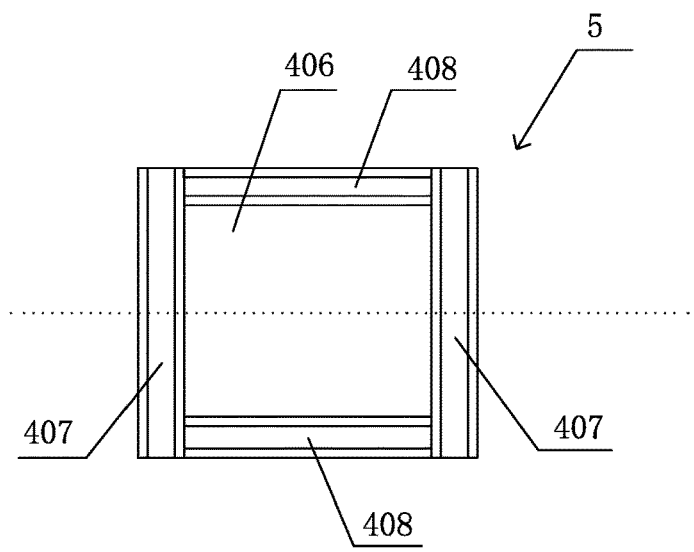
FIG. 12 is a schematic top view showing the structure of a second water-impermeable layer in the present invention.
Figure 13:
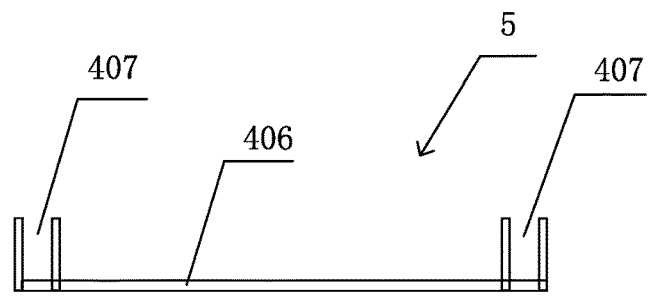
FIG. 13 is a schematic cross-sectional side view showing the structure of the second water-impermeable layer in the present invention.
Figure 14:
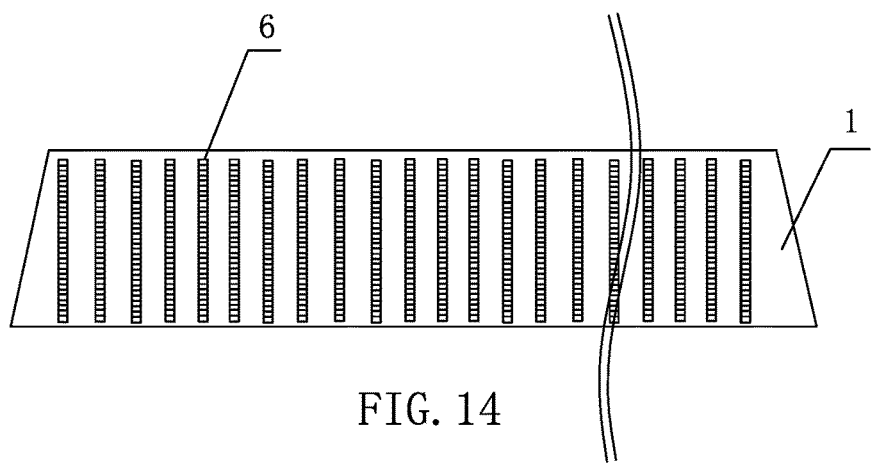
FIG. 14 is a schematic view showing the arrangement of third water-impermeable layers in the stacking site of the present invention.
Figure 15:
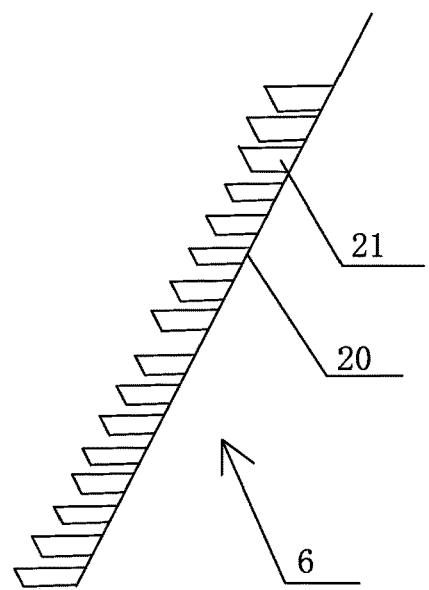
FIG. 15 is a schematic view showing the structure of the third water-impermeable layers in the present invention.
Figure 16:
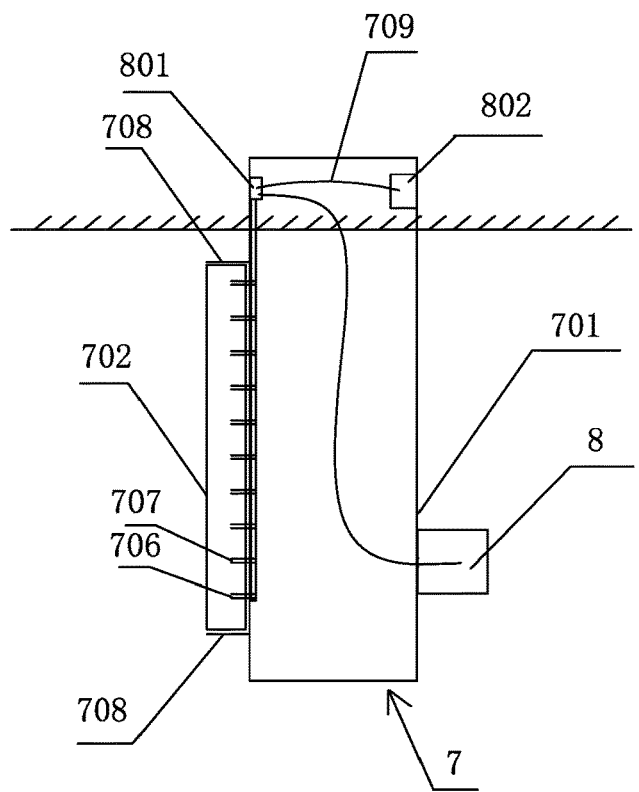
FIG. 16 is a schematic cross-sectional view showing the structure of a soil temperature and humidity monitor in the present invention.
Figure 17:
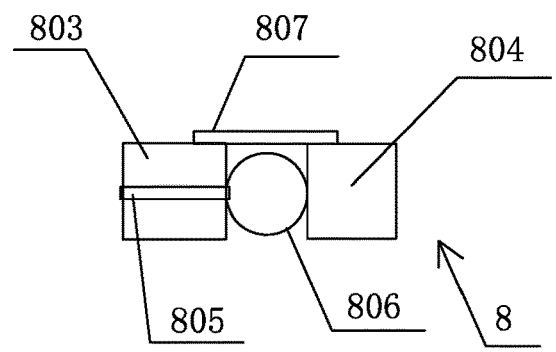
FIG. 17 is a schematic cross-sectional top view showing the structure of a cable tube in the present invention.
Figure 18:
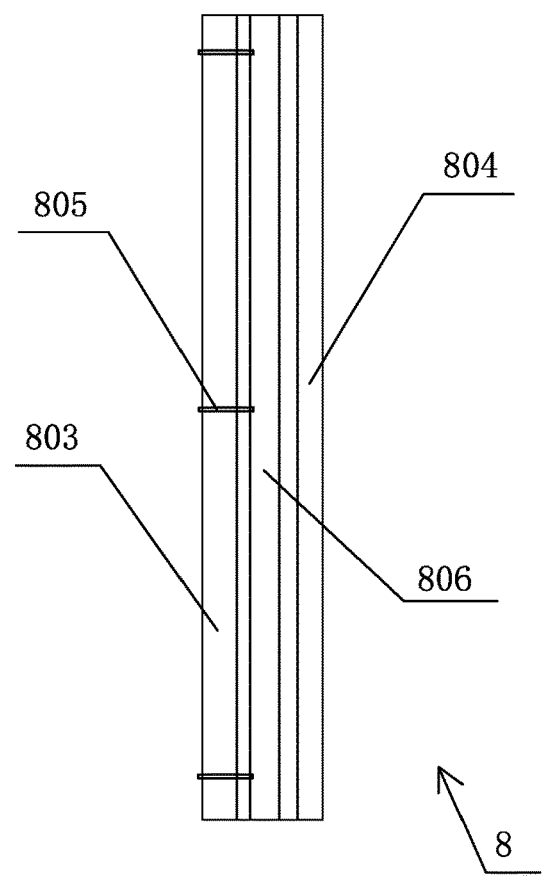
FIG. 18 is a schematic cross-sectional side view showing the structure of the cable tube in the present invention.
Figure 19:
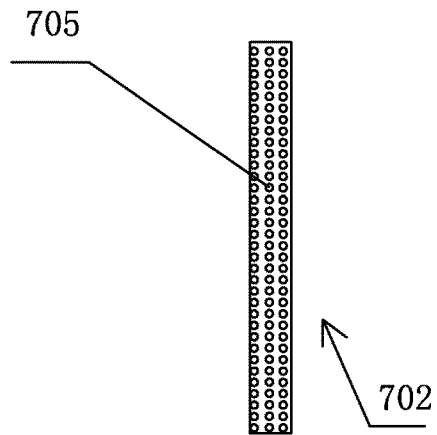
FIG. 19 is a top view of a soil monitoring tube in the present invention.
Figure 20:
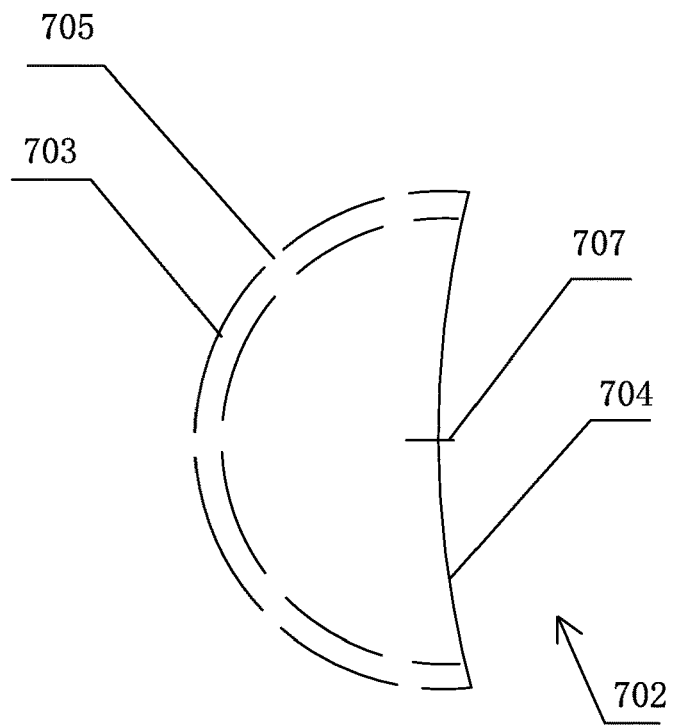
FIG. 20 is a schematic cross-sectional top view showing the structure of the soil monitoring tube in the present invention.

As shown in FIGS. 1 to 7 and 9 to 20, a real-time water-level monitoring system for a dumping site of an open-pit coal mine is provided. The dumping site of the open-pit coal mine includes an aboveground part and an underground part, where the aboveground part is a stacking site 1 located above an original ground surface. The real-time water-level monitoring system for a dumping site of an open-pit coal mine includes a first measuring well 2, and a second measuring well 3.

The first measuring well 2 is arranged vertically at the center of the stacking site 1 and formed by connecting a plurality of self-sealing sleeves 15 from top to bottom, in which an uppermost self-sealing sleeve 15 is provided with a breathable water-proof cover. The second measuring well 3 includes a vertical section 301, a horizontal section 302, and a free section 303 connected in sequence. The vertical section 301 is a drill hole provided under ground, the horizontal section 302 is formed by connecting self-sealing sleeves 15 from left to right and provided between the stacking site 1 and the original ground surface, and the free section 303 is provided vertically outside of the stacking site 1.

A first water-impermeable layer 4, a second water-impermeable layer 5 and a third water-impermeable layer 6 are provided internally in the stacking site 1, in which a plurality of soil temperature and humidity monitors 7 is provided on the first water-impermeable layer 4, and a plurality of automatic sprinklers 22 is provided on an upper surface and a slope of the stacking site 1.

The above structure is sufficient to achieve the objective of the present invention. On the basis of this, the present invention further provides the following preferred embodiments.

The first measuring well 2 is arranged at the center of the stacking site 1, and mainly configured to measure the changes in water level of the stacking site 1. The first measuring well 2 has a first water-level sensor 9 provided in a lower part and a fixing sleeve 10 provided in an upper part thereof. A coil cart 11 is provided above the stacking site 1, on which a first wireless transmission module is provided. The first water-level sensor 9 is connected to one end of a first cable 12, and the other end of the first cable 12 runs through the fixing sleeve 10 and is connected to the first wireless transmission module.

In the second measuring well 3, a fixed pulley is provided at a junction between the vertical section 301 and horizontal section 302, a second water-level sensor 13 is provided in a lower part of the vertical section 301, and the second water-level sensor 13 is connected through a second cable 14 to a second wireless transmission module located outside the free section free section 303.

The self-sealing sleeve 15 is formed by two hollow tubes of different diameters that are fixed by sleeved connection, and has identical bottom inner diameter and top outer diameter. The self-sealing sleeves 15 are positioned during the stacking process, which mainly function herein to form the first measuring well 2. The measuring well is previously formed by drilling manually. Herein, the measuring well is formed by installing the self-sealing sleeves 15, where one self-sealing sleeve 15 is installed first; and during the stacking process, the stacking site is gradually elevated, and another self-sealing sleeve 15 is installed when the elevation approaches a maximum height at which the installed self-sealing sleeve 15 is almost buried, and so on. In this way, the first measuring well 2 is formed.

The fixing sleeve 10 is cylindrical, a plurality of first grooves 16 depressed inwardly is provided on an outer side wall of the fixing sleeve 10, and a top-to-bottom through-hole 19 is provided at the center of the fixing sleeve 10. The fixing sleeve 10 mainly serves to fix the cable and ensure that the position of the first water-level sensor 9 is maintained unchanged. Therefore, when the coil cart 11 moves along the ground surface, no influence will be caused to the first water-level sensor 9. Moreover, the fixing sleeve 10 is not round shaped, and has no influence on the changes of water level in the well. The fixing sleeve 10 and the self-sealing sleeve 15 are fixed by a plastic therebetween. A first cable slit (17) that brings the interior and exterior of the self-sealing sleeve 15 into communication is provided on the self-sealing sleeve 15. A second cable slit 18 that brings the interior and exterior of the fixing sleeve 10 into communication is provided on the fixing sleeve 10. The through-hole 19 serves to fix the first cable 12, and the first cable 12 may be placed therein through the second cable slit 18.

The first water-level sensor 9 and the second water-level sensor 13 are a sensor connected to an external power supply and amenable to voltage transformation internally, and comprise internally, from bottom to top, a pressure probe 901, a transformer 902 and a first single chip microcomputer 903 connected in sequence. The first single chip microcomputer 903 is further connected to the pressure probe 901. A second groove 904 depressed upwardly is provided at a bottom of the first water-level sensor 9 and the second water-level sensor 13. A top of the second groove 904 corresponds to a bottom of the pressure probe 901. The transformer 902 is connected to an external power supply. The water pressure can be sensed by a hole formed by the second groove 904, and the sensing hole can be protected from being clogged by sand and stone in the well through such a design.

The fixed pulley comprises a pulley support rod and a pulley connected to the pulley support rod. The pulley has a diameter of 30 mm, and a width of 25 mm. The pulley support rod is 60 mm long, disposed vertically and soldered to an inner wall of the horizontal section 302.

The second measuring well 3 mainly serves to measure changes of water level below the original ground surface. Before stacking of the stacking site 1, a hole is drilled to form the vertical section 301; the horizontal section 302 is formed by connecting self-sealing sleeves 15 from left to right, and provided between the stacking site 1 and the original ground surface; and the free section 303 is made of a hollow rubber material and provided vertically outside of the stacking site 1. By virtue of such a design, communication with the atmosphere and the accurate work of the second water-level sensor 13 are ensured. Meanwhile, the free section 303 can move freely, without being affected by the stacking of the stacking site 1. Generally, the free section 303 is in a vertical state, and is 5 m or more in height, to ensure that no water comes out at a maximum water level.

The real-time water-level monitoring system for a dumping site of an open-pit coal mine according to the present invention further comprises a control center, in communication connection with the first wireless transmission module and the second wireless transmission module respectively.

The first measuring well 2 has a bottom that is 5-8 m away from the original ground surface, and a round cross section that is 80 mm in diameter. The length of the first cable 12 is 30 m longer than the height of the stacking site 1. The vertical section 301 of the second measuring well 3 is a drill hole that is 80 mm in diameter, and has a height that is 40 m higher than 1.2 times of the pit depth. The height of the free section 303 is 3 m or higher. The coil cart 11 can move freely in an extent of 10 m in diameter, which is convenient for pushing the soil by a bulldozer on the ground. The bottom of the fixing sleeve 10 is 40 m away from the original ground surface. The width of the first cable slit 17 and the second cable slit 18 is 15 mm. The diameter of the through hole 19 of the fixing sleeve 10 is 15 mm. The self-sealing sleeve 15 has a middle portion with an outer diameter of 94 mm and an inner diameter of 80 mm, a bottom portion with an outer diameter of 94 mm and an inner diameter of 87 mm, and a top portion with an outer diameter of 87 mm and an inner diameter of 80 mm. The fixing sleeve 10 is made of high strength plastic, and the self-sealing sleeve 15 is made of steel.

The breathable water-proof cover mainly serves to prevent the entering of sand and water caused by human work, and wind, rain and other natural factors in the vicinity and thus the influence on the measurement results, and remains breathable to communicate with the external atmosphere. The breathable water-proof cover comprises a cover body 101 and a fixed side guard plate 102 and an ash-damping side guard plate 103 secured to a bottom thereof. The cover body 101 is round, and the fixed side guard plate 102 and the ash-damping side guard plate 103 are a hollow cylinder. The fixed side guard plate 102 has a diameter less than that of the ash-damping side guard plate 103, and the fixed side guard plate 102 has a plurality of ventilation holes 104 provided at an upper portion thereof, and has a lower end removably fixedly connected to the self-sealing sleeves 15. The ash-damping side guard plate 103 mainly serves to make sure that the surrounding sand and water will not travel through the ventilation holes 104 and enter the drill hole. The cover body 101, the fixed side guard plate 102, and the ash-damping side guard plate 103 have an axis overlapped in a vertical direction. The fixed side guard plate 102 is screw connected to an upper end of the self-sealing sleeves 15.

The breathable water-proof cover is made of a high-strength resin material having high specific heat capacity, can resist the destruction from surrounding harsh environment, and also can reduce the vapor condensation in ambient air and other processes occurring upon their own cooling and warming up, to ensure the scientificity of the measurement data. The fixed side guard plate 102 has an inner diameter of 94 mm, an outer diameter of 100 mm, a height of 120 mm, and a lower screw region with a height of 30 mm. The length and height of the ventilation hole 104 are 80 and 60 mm respectively. The ash-damping side guard plate 103 has an inner diameter of 140 mm, an outer diameter of 145 mm, and a height of 200 mm. The cover body 101 has a diameter of 145 mm, and a height of 25 mm. A slant water baffle 105 has a slope of 150 mm in length, and a thickness of 3 mm. A water conduit 106 is 1.5 m in length.

The first water-impermeable layer 4 is rectangular and horizontally arranged inside the stacking site 1. The second water-impermeable layer 5 is a square water tank, and multiple second water-impermeable layers are present, which are arranged evenly above the first water-impermeable layer 4. The third water-impermeable layer 6 is arranged at a position close to the slope around the stacking site 1. The first water-impermeable layer 4 includes a rectangular waterproof resin soft board layer 401 and an anti-sliding water blocking means connected to a perimeter thereof. The anti-sliding water retaining means includes a horizontal water retaining plate 402, a plurality of vertical water retaining plates 403 arranged in parallel, and a plurality of anti-sliding plates 404 arranged in parallel. The horizontal water retaining plate 402 is connected to bottoms of the plurality of vertical water retaining plate 403 to form a plurality of water-retaining tank 405. The anti-sliding plate 404 is obliquely arranged, an upper end of which is connected to a bottom of the horizontal water retaining plate 402.

A plant having a long root system is planted on the first water-impermeable layer 4. The waterproof resin soft board layer 401, the horizontal water retaining plate 402, the vertical water retaining plate 403, and the anti-sliding plate 404 are all formed by waterproof resin soft boards. The waterproof resin soft board layer 401 is formed by joining a waterproof resin soft board which is one of (I) a commercially available PVC transparent soft board, and (II) a waterproof resin soft board produced through a process comprising: stirring 100 g of dimethyl terephthalate, 80 g of methylstyrene, 10 g of tribasic lead sulfate and 10 g of light calcium carbonate under an inert gas atmosphere while the temperature is maintained at 120° C., adding 1.5 g of palmitic acid, 1.5 g of barium palmitate and 5 g of a catalyst after fully stirring, and finally standing at room temperature for film formation.

For the self-made material, it is not necessary to consider the transparency. The transparency and other properties of the commercially available products are often taken into consideration. However, in the present invention, the material is usually buried under the ground, so the transparency and the turbidity have no need to be considered and the cost is much low. Moreover, the self-made product has a wear resistance better than the commercial product at the same thickness, and thus has an improved service life. As shown in an abrasion resistance test by the RCA tape abrasion test machine, an uncoated tape is scrolled to rub a sample under a load of 175 g, the substrate is exposed after 340 rounds in case of the PVC paint, and the substrate is exposed after 420 rounds in case of the self-made product. Therefore, the latter has a better wear resistance, and thus the service life is improved.

The second water-impermeable layer 5 include a large water tank 406, first small water tanks 407 connected left and right to the large water tank 406, and second small water tanks 408 connected before and after the large water tank 406. A plant having a short root system is planted on the second water-impermeable layer 5.

The third water-impermeable layer 6 includes a waterproof resin hard board 20 and a plurality of water conservation troughs 21 evenly fixed thereon. The waterproof resin hard board 20 is obliquely arranged to parallel the slop of the stacking site 1. A plurality of water conservation troughs 21 of boat shape is horizontally arranged between the slop of the stacking site 1 and the waterproof resin hard board 20, one end of which is fixed onto the waterproof resin hard board 20.

multiple third water-impermeable layers 6 are present, which are arranged evenly along the slope around the stacking site 1, a plurality of the third water-impermeable layer 6 that is on the same side is arranged in parallel, and an interval exists between adjacent two of the third water-impermeable layer 6. The waterproof resin hard board 20 is one of:

(I) a commercially available epoxy glass fiber board; and (II) a waterproof resin hard board prepared through a process comprising: stirring 100 g of dimethyl terephthalate, 80 g of methylstyrene, 10 g of tribasic lead sulfate and 10 g of light calcium carbonate under an inert gas atmosphere while the temperature is maintained at 120° C., adding 1.5 g of stearic acid, 1.5 g of barium stearate, and 5 g of a catalyst after fully stirring, and finally standing at room temperature for film formation.

For the self-made material, it is not necessary to consider the transparency. The transparency and other properties of the commercially available products are often taken into consideration. However, in the present invention, the material is usually buried under the ground, so the transparency and the turbidity have no need to be considered and the cost is much low. Moreover, the self-made product has a wear resistance better than the commercial product at the same thickness, and thus has an improved service life. As shown in an abrasion resistance test by the RCA tape abrasion test machine, an uncoated tape is scrolled to rub a sample under a load of 175 g, the substrate is exposed after 340 rounds in case of the PVC paint, and the substrate is exposed after 420 rounds in case of the self-made product. Therefore, the latter has a better wear resistance, and thus the service life is improved.

The plant having a long root system is one or more of: fruit trees, sweet potatoes, soybeans, potatoes, peanuts, and soya beans. The plant having a short root system is one or more of: *Paspalum natatu, Festuca elata, Poa annua, Zoysia pacifica, Hippeastrum rutilum, Celosia cristata* L., *S. rebaudiana, Gardenia jasminoides, Sago palm, Citrus reticulata*, and *Michelia figo*.

The first water-impermeable layer 4 is 1.1 m away from the top surface of the stacking site 1, and a horizontal distance from each side to the side surface of the stacking site 1 is 6 m. The distances from the vertical water retaining plate 403 to two adjacent vertical water retaining plate 403 are both 300 mm. The width of the horizontal water retaining plate 402 is 15 mm. The waterproof resin soft board layer 401 is 7 mm in thickness. The anti-sliding plate 404 has a thickness of 10 mm, a width of 200 mm, and a length identical to that of the water-retaining tank 405. The distance between two adjacent anti-sliding plates 404 is 450 mm, and the angle of the anti-sliding plate 404 to the horizontal place is 30°. The top ends of the anti-sliding plates 404 are positioned towards the center of the waterproof resin soft board layer 401, that is, the anti-sliding plates are configured to have a radial structure.

The second water-impermeable layer 5 is 2 m in both the length and the width, and 0.15 m in height, and the distance between two adjacent second water-impermeable layers 5 is 2 m. The large water tank 406 is 1800 mm long, 1800 mm wide and 150 mm high. The first small water tank 407 is 100 mm long, 2000 mm wide and 150 mm high. The second small water tank 408 is 1800 mm long, 100 mm wide and 150 mm high.

The waterproof resin hard board 20 is 5 m long, 2 m wide, and 10 mm thick, and the distance between two adjacent waterproof resin hard boards 20 is 2.5 m. The water conservation trough 21 is of boat shape, and has a depth of 100 mm, a lower portion that is 150 mm wide and 2 m long, and an upper portion that is 200 mm wide and 2 m long. The distance between two adjacent water conservation troughs 21 in the vertical direction is 0.5 m.

The dimension and structure of the water conservation trough 21 are designed to ensure that the side area of the entire stacking site can meet the water storage requirements and that the slope is table because the friction on the side surface of the stacking site 1 will not be decreased by the third water-impermeable layer. The dimension and structure of the first water-impermeable layer 4 are designed to ensure that the water is blocked from leaking downward, and that the region of the stacking site 1 closed to the side surface has a much higher shear strength and is thus more stable.

The soil temperature and humidity monitor 7 comprises a barrel 701 and a slot 708 connected to an outer wall thereof, and a soil monitoring tube 702 is disposed in the slot 708. The soil monitoring tube 702 is elongate, and formed by a first arc-shaped sidewall 703 and a second arc-shaped sidewall 704 depressed towards the same direction. Two ends of the first arc-shaped sidewall 703 are connected to two ends of the second arc-shaped sidewall 704. A plurality of seepage holes 705 is provided on the first arc-shaped sidewall 703, and a plurality of probe holes through which electrode probes pass is provided on the second arc-shaped sidewall 704. A plurality of pairs of the electrode probes runs through the second arc-shaped sidewall 704 and the wall of the barrel 701. The electrode probes comprise a plurality of pairs of temperature probes 706 and a plurality of pairs of humidity probes 707. A second single chip microcomputer 801 and a wireless transmission means 802 connected via a data line 709 sequentially to the electrode probe are fixed on an inner wall at an upper portion of the barrel 701. A third cable hole is provided at a lower portion of the barrel 701, and the second single chip microcomputer 801 is further connected to a cable tube 8.

The first arc-shaped sidewall 703 is of an obtuse-angled arc shape having a cross section of 40 mm in diameter and a central angle of 219°, and the second arc-shaped sidewall 704 is of an acute-angled arc shape having a cross section of 60 mm in diameter and a central angle of 77°. The slot 708 is formed by an upper iron plate and a lower iron plate that fully cover the cross section of the soil monitoring tube 702.

The cable tube 8 is elongate and has a length direction that is perpendicular to a stacking direction of the stacking site 1. A plurality of the cable tube 8 is arranged in parallel above the water-impermeable layer 2, each cable tube 8 being connected with a plurality of the soil temperature and humidity monitors 7. The cable tube 8 comprises a second cable hole 806 and a left support block 803 and a right support block 804 disposed at both sides thereof. A head plate 807 is provided on a top of the second cable hole 806, and two sides of the head plate 807 are secured respectively to the left support block 803 and the right support block 804. A plurality of first cable holes 805 is evenly provided inside the left support block 803, an axial direction of the first cable hole 805 is perpendicular to an axial direction of the second cable hole 806, and the first cable hole 805 brings the exterior and the second cable hole 806 into communication. Tolerance to pressure and thus safety and stability of the cable are ensured by means of such a design.

Each cable tube 8 is connected with 3 soil temperature and humidity monitors 7. The number of the first cable holes 805 is 3, and can be adjusted according to practical demands, with 3 being preferred. The number of the electrode probes is 10 pairs, including 5 pairs of temperature probes 706 and 5 pairs of humidity probe 707, which are alternately arranged from top to bottom along a length direction of the soil monitoring tube 702. The number can be adjusted according to practical demands, and each 5 pairs are preferred.

The system of the present invention further comprises a power line, one end of which is connected to the second single chip microcomputer 801, and the other end of which extends sequentially through the third cable hole, the first cable hole 805 and the second cable hole 806, then exits from the side of the stacking site 1, and is connected to an industrial power supply, to ensure the powering by the power supply and the stability of the monitoring process. The pressure tolerant design of the cable tube 8 ensures the safety of the power line, and the industrial power supply ensures the power stability. Because lots of work is carried out on the surface of the stacking site 1, solar panel is unfeasible, and disposable lithium batteries are also unfeasible because of the high costs and the limited power. By contrast, the industrial power supply is stable, reliable, and cheap. A signal is wirelessly transmitted from the wireless transmission means 802 to the control center. Because lots of work is carried out on the surface of the stacking site 1, wireless transmission is necessitated. The automatic sprinklers 22 are controlled to spray water by the control center.

A plurality of automatic sprinklers 22 are evenly provided on the upper and side surfaces of the stacking site 1, and the control center is in communication connection with the wireless transmission means 802 and the automatic sprinklers 22. The distance between adjacent two cable tubes 8 is 60 m. The barrel 701 is 1.2 m high, and has an upper end that is 0.2 m higher than the surface of the stacking site 1, and a lower end that is 0.1 m away from the first water-impermeable layer 4. The soil monitoring tube 702 is 0.7 m high, and is 0.2 m away from the surface of the stacking site 1 and the first water-impermeable layer 4. That is, the temperature and humidity from 0.2 m to 0.9 m beneath the ground surface are monitored. This region is also a region of the dumping site where the root system is developed.

Embodiment 2

Figure 8:
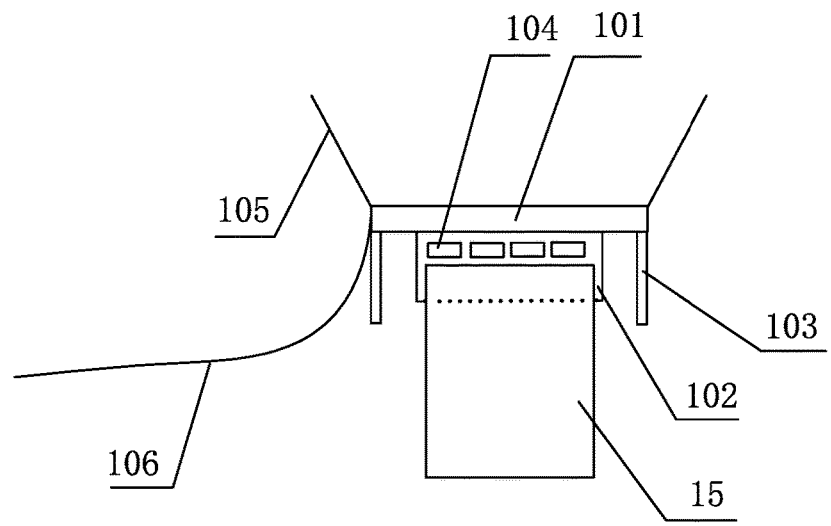
FIG. 8 is a schematic view showing the structure of a breathable water-proof cover in Embodiment 2 of the present invention.

As shown in FIGS. 1 to 6, and 8 to 20, on the basis of Embodiment 1, the breathable water-proof cover in this embodiment further has a structure as shown below.

A slant water baffle 105 of cylindrical shape with a diameter decreasing gradually from top to bottom is connected to an upper end of the cover body 101, and the slant water baffle 105 is at an angle of 115° with respect to the cover body 101. An upper end of the water conduit 106 is connected at a junction between the slant water baffle 105 and the cover body 101, and a lower end of the water conduit 106 is in communication with a region that is 1 m away from the first measuring well 2. The other structures are the same as those in Embodiment 1.

Embodiment 3

As shown in FIGS. 1 to 7, and 9 to 20, on the basis of Embodiment 1, this embodiment further has a structure as shown below.

A plurality of first soil humidity sensors are fixed on the waterproof resin soft board layer 401. A second soil humidity sensor is fixed on some of the second water-impermeable layers 5. 3 third soil humidity sensors are provided on every $5^{th}$ or $6^{th}$ third water-impermeable layer 6, which are fixed onto the uppermost, the middle, and the lowermost water conservation troughs 21. It can be seen that not all of the third water-impermeable layers 6 are fitted with the third soil humidity sensors, and the third soil humidity sensors are fitted only on some water conservation troughs 21 of a small number of the third water-impermeable layers 6. In this way, a good monitoring effect is achieved, and the cost is saved.

The distance between two adjacent first soil humidity sensors and two adjacent second soil humidity sensors is 50 m. It can be seen that not all, but some of the second water-impermeable layers 5 are fitted with the second soil humidity sensors. In this way, the purpose is achieved and the cost is saved.

The other structures are the same as those in Embodiment 1.

Embodiment 4

A method for establishing and using the real-time water-level monitoring system for a dumping site of an open-pit coal mine is provided, which comprises the steps of (A) finding a position at a center of the dumping site based on design drawings, drilling a hole to form the vertical section 301 of the second measuring well 3 in which the second water-level sensor 13 is disposed, disposing the horizontal section 302, and arranging the second cable 14, to monitor the changes of water level;

(B) after 2 to 3 months, mining the working face of the open-pit coal mine and stripping the topsoil of the mine area onto the stacking site 1; laying the self-sealing sleeve (15) when the stacking site 1 is gradually stacked to a height of 5-8 m, to form the first measuring well (2), and at the same time, installing the free section 303 to a lateral end of the horizontal section 302, in which the free section 303 is a rubber tube formed by means of irrigation;

(C) after 3 to 5 months, beginning to monitor the water level in the first measuring well 2 when the stacking site 1 is gradually stacked to a height of 40 m, in which the first water-level sensor 9 is installed, and installing and affixing the fixing sleeve 10 at the inlet, to make sure that the first cable 12 and the first water-level sensor 9 under the fixing sleeve 10 is not affected by activities above the well top;

(D) pushing an area from an edge of the stacking site 1 to a position that is 6 m inward into a plane of 18-25° by a bulldozer after 1 to 2 years when a middle area of the stacking site 1 in this region has a height that is 1.1 m lower than the maximum stacking height; laying the first water-impermeable layer 4, in which a plurality of waterproof resin soft boards is spliced to form the waterproof resin soft board layer 401 at the top of the stacking site 1, an edge of which is 6 m away from an edge of the stacking site 1 at the top; laying the anti-sliding water blocking means at the edge of the waterproof resin soft board layer 401, where if the anti-sliding water blocking means is spliced to the waterproof resin soft board, sealing is needed; the first water-impermeable layer 4 is sealedly connected to the self-sealing sleeve 15; and after the first cable 12 is inserted into the self-sealing sleeve 15 above the first water-impermeable layer 4, the first cable slit 17 is manually sealed;

(E) providing the soil temperature and humidity monitors 7 on the first water-impermeable layer 4 at a longitudinal and horizontal interval of 50 m, laying a cable tube (8) at a designed position, laying the power line, laying the barrel 701 and the soil monitoring tube 702, stacking the soil continuously, and artificially leveling and compacting until uniform in the vicinity of the barrel 701 and the soil monitoring tube 702;

(F) installing the self-sealing sleeve 15 that is calculated to be the last segment, fixing the first cable 12, sealing all the first cable slits 17 above the surface of the stacking site 1, and covering the breathable water-proof cover;

(G) after the stacking site 1 has reached the maximum stacking height, laying the third water-impermeable layers 6 at an interval of 2.5 m on the rear side and on both sides of the stacking site, pouring sand and soil slowly at the interval between the third water-impermeable layers 6, and manually plastering until uniform, to ensure that the slant surface is elevated outward by 0.7 m along the horizontal direction;

(H) after the stacking site is stacked, laying a 300 mm-thick surface humus soil collected from the original ground surface on the upper surface and the side surfaces, spraying water, and properly dusting some fertilizer; and planting a plant of drought-resistant species having a short root system previously grown locally right above the second water-impermeable layer 5, or, if such a plant does not exist, or is difficult to grow, planting one or more of: *Paspalum natatu, Festuca elata, Poa annua, Zoysia pacifica, Hippeastrum rutilum, Celosia cristata* L., *S. rebaudiana, Gardenia jasminoides, Sago palm, Citrus reticulata,* and *Michelia figo*, where the position at which the plant is to be planted is right above the second water-impermeable layer (5), and the plating area is 2×2 m; and planting a plant of drought-resistant species having a long root system previously grown locally in other areas of the stacking site 1, or, if such a plant does not exist, or is difficult to grow, planting one or more of: fruit trees, sweet potatoes, soybeans, potatoes, peanuts, and soya beans; and planting a plant of drought-resistant species having a short root system previously grown locally in the side area, or, if such a plant does not exist, or is difficult to grow, planting one or more of: *Vetiveria zizanoides, Paspalum natatu,* and *Poa annua;*

(I) fully monitoring the water level in the stacking site 1 and the water level of the ground water, and performing comprehensive analysis on the data; when the water level in the first measuring well 2 reaches 3.5 m, which is mainly caused by replenishment of surface water such as rainfall, well carrying out the safety patrol work of the dumping site uninterruptedly especially in the slope region, to prevent the injury and damage to the surrounding persons and property caused by landslides; preventing the gushing-out of water from the pit, and well performing the relevant early warning and investigation work; or when the water level declines or rises at a rate that is 1.5 times or more faster than a previous day, which is a chronic variation trend in the water level caused by the mining events or water flow events, analyzing the reasons and eliminating the potential risks timely; and (J) when any pair of the humidity probes 707 at a monitoring point show that the soil humidity is less than 19%, the data being automatically transmitted to the automatic sprinklers 22, and the automatic sprinkler 22 in this region spraying water; when 5 pairs of the humidity probes 707 show that the soil humidity is greater than 30% or 1 pair of the humidity probes 707 show that the soil humidity reaches 42%, the automatic sprinklers 22 stopping spraying water; when the uppermost humidity probe 707 generally showing a minimum humidity shows that the soil humidity is less than 19%, the automatic sprinkler 22 in this region spraying water at a radius of 6 m; when the humidity probes 707 monitoring that the soil humidity is less than 19% are the $2^{nd}$, $3^{rd}$, $4^{th}$, and $5^{th}$ probes from top to bottom, the automatic sprinklers 22 spraying water at a radius of 8 m, 11 m, 15 m, and 20 m respectively; and when 5 pairs of humidity probes 707 show that the soil humidity is greater than 30% or 1 pair of the humidity probes 707 show that the soil humidity reaches 42%, the automatic sprinklers 22 stopping spraying water.

The foregoing embodiments are merely illustrative of preferred embodiments of the present invention and are not intended to limit the scope of the present invention. Various variations and modifications made to the technical solutions of the present invention by those skilled in the art without departing from the spirit of the present invention are embraced in the protection scope of the present invention as defined by the appended claims.

What is claimed is:

1. A real-time water-level monitoring system for a dumping site of an open-pit coal mine, the dumping site of the open-pit coal mine comprising an aboveground part and an underground part and the aboveground part being a stacking site (1) located above an original ground surface, the real-time water-level monitoring system for a dumping site of an open-pit coal mine comprising a first measuring well (2), and a second measuring well (3), wherein the first measuring well (2) is arranged vertically at a center of the stacking site (1) and formed by connecting a plurality of self-sealing sleeves (15) from top to bottom, in which an uppermost self-sealing sleeve (15) is provided with a breathable water-proof cover; and the second measuring well (3) comprises a vertical section (301), a horizontal section (302), and a free section (303) connected in sequence, in which the vertical section (301) is a drill hole provided under ground, the horizontal section (302) is formed by connecting self-sealing sleeves (15) from left to right, and provided between the stacking site (1) and the original ground surface, and the free section (303) is provided vertically outside of the stacking site (1); and a first water-impermeable layer (4), a second water-impermeable layer (5), and a third water-impermeable layer (6) are provided internally in the stacking site (1), in which a plurality of soil temperature and humidity monitors (7) is provided on the first water-impermeable layer (4), and a plurality of automatic sprinklers (22) is provided on an upper surface and a slope of the stacking site (1).

2. The real-time water-level monitoring system for a dumping site of an open-pit coal mine according to claim 1, wherein the first measuring well (2) has a first water-level sensor (9) provided in a lower part and a fixing sleeve (10) provided in an upper part thereof, and a coil cart (11) is provided above the stacking site (1) on which a first wireless transmission module is provided, where the first water-level sensor (9) is connected to one end of a first cable (12), and the other end of the first cable (12) runs through the fixing sleeve (10) and is connected to the first wireless transmission module; and in the second measuring well (3), the free section (303) is made of a hollow rubber material, a fixed pulley is provided at a junction between the vertical section (301) and the horizontal section (302), a second water-level sensor (13) is provided in a lower part of the vertical section (301), and the second water-level sensor (13) is connected through a second cable (14) to a second wireless transmission module located outside the free section (303).

3. The real-time water-level monitoring system for a dumping site of an open-pit coal mine according to claim 2, wherein the self-sealing sleeve (15) is formed by two hollow tubes of different diameters that are fixed by sleeved connection, and has identical bottom inner diameter and top outer diameter; and a first cable slit (17) that brings the interior and exterior of the self-sealing sleeve (15) into communication is provided on the self-sealing sleeve (15);

the fixing sleeve (10) is cylindrical, a plurality of first grooves (16) depressed inwardly is provided on an outer side wall of the fixing sleeve (10), a top-to-bottom through-hole (19) is provided at the center of the fixing sleeve (10), and the fixing sleeve (10) and the self-sealing sleeve (15) are fixed by a plastic therebetween; and a second cable slit (18) that brings the interior and exterior of the fixing sleeve (10) into communication is provided on the fixing sleeve (10);

the first water-level sensor (9) and the second water-level sensor (13) comprise internally, from bottom to top, a pressure probe (901), a transformer (902) and a first single chip microcomputer (903) connected in sequence, where the first single chip microcomputer (903) is further connected to the pressure probe (901), a second groove (904) depressed upwardly is provided at a bottom of the first water-level sensor (9) and the second water-level sensor (13), a top of the second groove (904) corresponds to a bottom of the pressure probe (901), and the transformer (902) is connected to an external power supply;

the fixed pulley comprises a pulley support rod and a pulley connected to the pulley support rod, where the pulley has a diameter of 30 mm, and a width of 25 mm, the pulley support rod is 60 mm long, disposed vertically and soldered to an inner wall of the horizontal section (302); and the real-time water-level monitoring system for a dumping site of an open-pit coal mine further comprises a control center, in communication connection with the first wireless transmission module and the second wireless transmission module respectively.

4. The real-time water-level monitoring system for a dumping site of an open-pit coal mine according to claim 3, wherein the soil temperature and humidity monitor (7) comprises a barrel (701) and a slot (708) connected to an outer wall thereof, and a soil monitoring tube (702) is disposed in the slot (708), where the soil monitoring tube (702) is elongate, and formed by a first arc-shaped sidewall (703) and a second arc-shaped sidewall (704) depressed towards the same direction, two ends of the first arc-shaped sidewall (703) are connected to two ends of the second arc-shaped sidewall (704), a plurality of seepage holes (705) is provided on the first arc-shaped sidewall (703), and a plurality of probe holes through which electrode probes pass is provided on the second arc-shaped sidewall (704); a plurality of pairs of the electrode probes runs through the second arc-shaped sidewall (704) and the wall of the barrel (701), and the electrode probes comprise a plurality of pairs of temperature probes (706) and a plurality of pairs of humidity probes (707); a second single chip microcomputer (801) and a wireless transmission means (802) connected via a data line (709) sequentially to the electrode probe are fixed on an inner wall at an upper portion of the barrel (701), a third cable hole is provided at a lower portion of the barrel (701), and the second single chip microcomputer (801) is further connected to a cable tube (8).

5. The real-time water-level monitoring system for a dumping site of an open-pit coal mine according to claim 4, wherein the first arc-shaped sidewall (703) is of an obtuse-angled arc shape having a cross section of 40 mm in diameter and a central angle of 219°, and the second arc-shaped sidewall (704) is of an acute-angled arc shape having a cross section of 60 mm in diameter and a central angle of 77°; and the slot (708) is formed by an upper iron plate and a lower iron plate that fully cover the cross section of the soil monitoring tube (702);

the cable tube (8) is elongate and has a length direction that is perpendicular to a stacking direction of the stacking site (1), and a plurality of the cable tubes (8) is arranged in parallel above the first water-impermeable layer (4), each cable tube (8) being connected with a plurality of the soil temperature and humidity monitors (7);

the cable tube (8) comprises a second cable hole (806) and a left support block (803) and a right support block (804) disposed at both sides thereof; a head plate (807) is provided on a top of the second cable hole (806), and two sides of the head plate (807) are secured respectively to the left support block (803) and the right support block (804); and a plurality of first cable holes (805) is evenly provided inside the left support block (803), an axial direction of the first cable hole (805) is perpendicular to an axial direction of the second cable hole (806), and the first cable hole (805) brings the exterior and the second cable hole (806) into communication; and the system further comprises a power line, one end of which is connected to the second single chip microcomputer (801), and the other end of which extends sequentially through the third cable hole, the first cable hole (805), and the second cable hole (806) and then connected to an industrial power supply; and the control center is in communication connection with the wireless transmission means (802) and the automatic sprinklers (22).

6. The real-time water-level monitoring system for a dumping site of an open-pit coal mine according to claim 1, wherein the breathable water-proof cover comprises a cover body (101) and a fixed side guard plate (102) and an ash-damping side guard plate (103) secured to a bottom thereof, where the cover body (101) is round, the fixed side guard plate (102) and the ash-damping side guard plate (103) are a hollow cylinder, and the fixed side guard plate (102) has a diameter less than that of the ash-damping side guard plate (103); and the fixed side guard plate (102) has a plurality of ventilation holes (104) provided at an upper portion thereof, and has a lower end removably fixedly connected to the self-sealing sleeve (15).

7. The real-time water-level monitoring system for a dumping site of an open-pit coal mine according to claim 6, wherein the cover body (101), the fixed side guard plate (102), and the ash-damping side guard plate (103) have an axis overlapped in a vertical direction; the fixed side guard plate (102) is screw connected to an upper end of the self-sealing sleeve (15); a slant water baffle (105) of cylindrical shape with a diameter decreasing gradually from top to bottom is connected to an upper end of the cover body (101), and the slant water baffle (105) is at an angle of 115° with respect to the cover body (101); and an upper end of a water conduit (106) is connected at a junction between the slant water baffle (105) and the cover body (101), and a lower end of the water conduit (106) is in communication with a region that is 1 m away from the first measuring well (2).

8. The real-time water-level monitoring system for a dumping site of an open-pit coal mine according to claim 1, wherein the first water-impermeable layer (4) is rectangular and horizontally arranged inside the stacking site (1); the second water-impermeable layer (5) is a square water tank, and multiple second water-impermeable layers are present, which are arranged evenly above the first water-impermeable layer (4); and the third water-impermeable layer (6) is arranged at a position close to the slope around the stacking site (1).

9. The real-time water-level monitoring system for a dumping site of an open-pit coal mine according to claim 8, wherein the first water-impermeable layer (4) includes a rectangular waterproof resin soft board layer (401) and an anti-sliding water blocking means connected to a perimeter thereof, and the anti-sliding water retaining means includes a horizontal water retaining plate (402), a plurality of vertical water retaining plates (403) arranged in parallel, and a plurality of anti-sliding plates (404) arranged in parallel, in which the horizontal water retaining plate (402) is connected to bottoms of the plurality of vertical water retaining plates (403) to form a plurality of water-retaining tanks (405), and the anti-sliding plate (404) is obliquely arranged, an upper end of which is connected to a bottom of the horizontal water retaining plate (402);

the second water-impermeable layer (5) include a large water tank (406), first small water tanks (407) connected left and right to the large water tank (406), and second small water tanks (408) connected before and after the large water tank (406);

the third water-impermeable layer (6) include a waterproof resin hard board (20) and a plurality of water conservation troughs (21) evenly fixed thereon, where the waterproof resin hard board (20) is obliquely arranged to parallel the slope of the stacking site (1), and the plurality of water conservation troughs (21) of boat shape is horizontally arranged between the slope of the stacking site (1) and the waterproof resin hard board (20), one end of which is fixed onto the waterproof resin hard board (20); and multiple third water-impermeable layers (6) are present, which are arranged evenly along the slope around the stacking site (1), a plurality of the third water-impermeable layers (6) that is on the same side is arranged in parallel, and an interval exists between adjacent two of the third water-impermeable layer (6), where a plant having a long root system is planted on the first water-impermeable layer (4), and a plant having a short root system is planted on the second water-impermeable layer (5);

wherein the waterproof resin soft board layer (401), the horizontal water retaining plate (402), the vertical water retaining plate (403), and the anti-sliding plate (404) are all formed by waterproof resin soft boards which are PVC transparent soft boards or are produced through a process comprising: stirring 100 g of dimethyl terephthalate, 80 g of methylstyrene, 10 g of tribasic lead sulfate and 10 g of light calcium carbonate under an inert gas atmosphere while the temperature is maintained at 120° C., adding 1.5 g of palmitic acid, 1.5 g of barium palmitate and 5 g of a catalyst after fully stirring, and finally standing at room temperature for film formation; and the waterproof resin hard board (20) is an epoxy glass fiber board or is prepared through a process comprising: stirring 100 g of dimethyl terephthalate, 80 g of methylstyrene, 10 g of tribasic lead sulfate and 10 g of light calcium carbonate under an inert gas atmosphere while the temperature is maintained at 120° C., adding 1.5 g of stearic acid, 1.5 g of barium stearate, and 5 g of a catalyst after fully stirring, and finally standing at room temperature for film formation.

\* \* \* \* \*